United States Patent [19]
Gonzalez et al.

[11] Patent Number: 5,952,207
[45] Date of Patent: Sep. 14, 1999

[54] PROCESS OF PRODUCING WHEY PRODUCED AS A BY-PRODUCT OF CHEESE MANUFACTURE

[76] Inventors: Juan Fuertes Gonzalez, Rios Rosas, 17, 2 C., 28003 Madrid; Angela Maria Moya Mora, Pasaje San Vicente Ferrer, 1-3 B., 13004 Ciudad Real, both of Spain

[21] Appl. No.: 08/930,794

[22] PCT Filed: Jan. 13, 1997

[86] PCT No.: PCT/ES97/00006

§ 371 Date: Oct. 7, 1997

§ 102(e) Date: Oct. 7, 1997

[87] PCT Pub. No.: WO97/29204

PCT Pub. Date: Aug. 14, 1997

[30] Foreign Application Priority Data

Feb. 8, 1996 [ES] Spain ................................ 9600301

[51] Int. Cl.$^6$ ................................ C12P 7/56; A23C 9/12; A23C 21/00
[52] U.S. Cl. ................................ 435/139; 426/41; 426/42; 426/583; 435/819; 435/853; 435/856
[58] Field of Search ................................ 426/41, 42, 583; 435/139, 819, 853, 856

[56] References Cited

U.S. PATENT DOCUMENTS

| 3,818,109 | 6/1974 | Bechtle | 426/41 |
| 3,968,257 | 7/1976 | Muller | 426/41 |
| 4,676,987 | 6/1987 | Ahern et al. | 426/41 |
| 4,698,303 | 10/1987 | Bailey et al. | 435/139 |
| 4,699,793 | 10/1987 | Eguchi et al. | 426/41 |
| 5,210,294 | 5/1993 | Mantovani et al. | 562/580 |

FOREIGN PATENT DOCUMENTS 25555200  5/1985  France .

Primary Examiner—Leon B. Lankford, Jr.
Assistant Examiner—Christopher Tate
Attorney, Agent, or Firm—Gifford, Krass, Groh, Sprinkle, Anderson & Citkowski, P.C.

[57] ABSTRACT

A process of treating whey produced as a by-product of cheese manufacture is disclosed. The process eliminates the contaminating effects of proteins including albumin and globulins within the whey. The fermentation of the treated whey produces enantromerically enriched lactic acid.

17 Claims, 1 Drawing Sheet

PROCESS OF PRODUCING WHEY PRODUCED AS A BY-PRODUCT OF CHEESE MANUFACTURE

This application claims priority of Spanish patent application P9600301, filed Feb. 8, 1996.

FIELD OF THE INVENTION

As in stated in the heading above, this patent is related to a procedure for processing the whey which is produced as a by-product in the cheese-manufacturing industries, this being a by-product which constitutes a problem due to the contaminating features of its content, given that it is comprised of solid substances, particularly lactose, a readily-fermentable sugar, as well as a large number of microorganisms which might give rise to cases of undesirable fermentation.

DESCRIPTION OF THE RELATED ART

The effluents and disposal of the whey produced in the cheese-making industries are a serious problem given that the laws currently in force are aimed at protecting the environment.

In addition to affording the possibility of eliminating the undesirable contaminating effects of the aforesaid by-product, the implementation of this procedure is the object of this patent also provides the considerable advantage of obtaining such an industrially valuable product as L-lactic acid as a final resulting by-product.

It has been known for a long time that L-lactic acid is an essential additive in the food-preserving industry which is obtained by many known methods, some of which have been created specifically for the production thereof.

Starting in 1931, a lactobacillus was employed to produce L-lactic acid, that is, *Lactobacillus bulgaricus*, to carry out a suitable fermentation at a controllable pH. The lactic acid contained in the fermentation medium was later removed using sulphuric acid, giving rise to an acid suitable for use in the food industry.

The aforesaid method entailed major drawbacks, given that the full use of the sugar employed was limited to 80%, and the separation and purification methods gave rise to greater degrees of contamination than those they were aimed at correcting.

Therefore, procedures were subsequently further developed aimed at preventing the aforementioned drawbacks. One of these procedures is the object of French Patent No. 83 18631, which claims a continuous fermentation system entailing different stages in which organic acids and sugars are finally obtained in the end, but which turns out to be a too highly involved industrial process.

A later procedure was described in U.S. Pat. No. 4,698, 303, but which also entailed a major drawback on it being necessary to eliminate the proteins of relatively high molecular weights in order to obtain the lactic acid, additionally requiring that the whey be centrifuged and subsequently ultrafiltered, which gave rise to specific problems regarding the strength of the membranes employed, entailing a major reduction in efficiency and the need of employing removal techniques using different solvents, the recovery of which would involve added complications and cases of contamination.

Although the two aforementioned patents afford the possibility of obtaining a lactic acid of a purity sufficing for its use in the food industry and for the manufacture of pharmaceutical products, it can also be used in industrial processes less stringent as regards the quality of the lactic acid obtained, some of which may include the manufacture of mordants for tanning, the treatment of other surfaces and the processing of chemical products, as the most significant, unrestricted examples.

BRIEF SUMMARY OF THE INVENTION

We thus find that by employing the procedure comprising the object of this patent, two advantages which complement one another and which are, in turn, significantly valuable in themselves, are achieved. These advantages being the elimination of the contaminating effects of the whey produced as a by-product in cheese manufacture, as has been previously mentioned, and, secondly, the accomplishment of obtaining a by-product of industrial value and of high quality.

As regards the first of the aforesaid advantages, we are confronted with the need of eliminating solid substances existing in the whey, basically lactose, entailing percentages of 4.2%–4.7% of the contents, in a medium having a high moisture content (93%–94%) and, thus, under conditions greatly favoring cases of undesirable, uncontrolled fermentation taking place, on the bacteria count being quite high. Special mention must also be made of the possible presence in this whey of highly contaminating substances, such as nitrites and some highly toxic metal salts.

As regards the second advantage which is achieved, we can mention that it has been possible to develop a procedure which affords the possibility of achieving a lactic acid in which the proportion of L-lactic acid makes it particularly ideal for use in the food industry with assured quality and, due to its being processed as a by-product, under advantageous cost-related conditions.

DETAILED DESCRIPTION OF THE INVENTION

Figure 1:
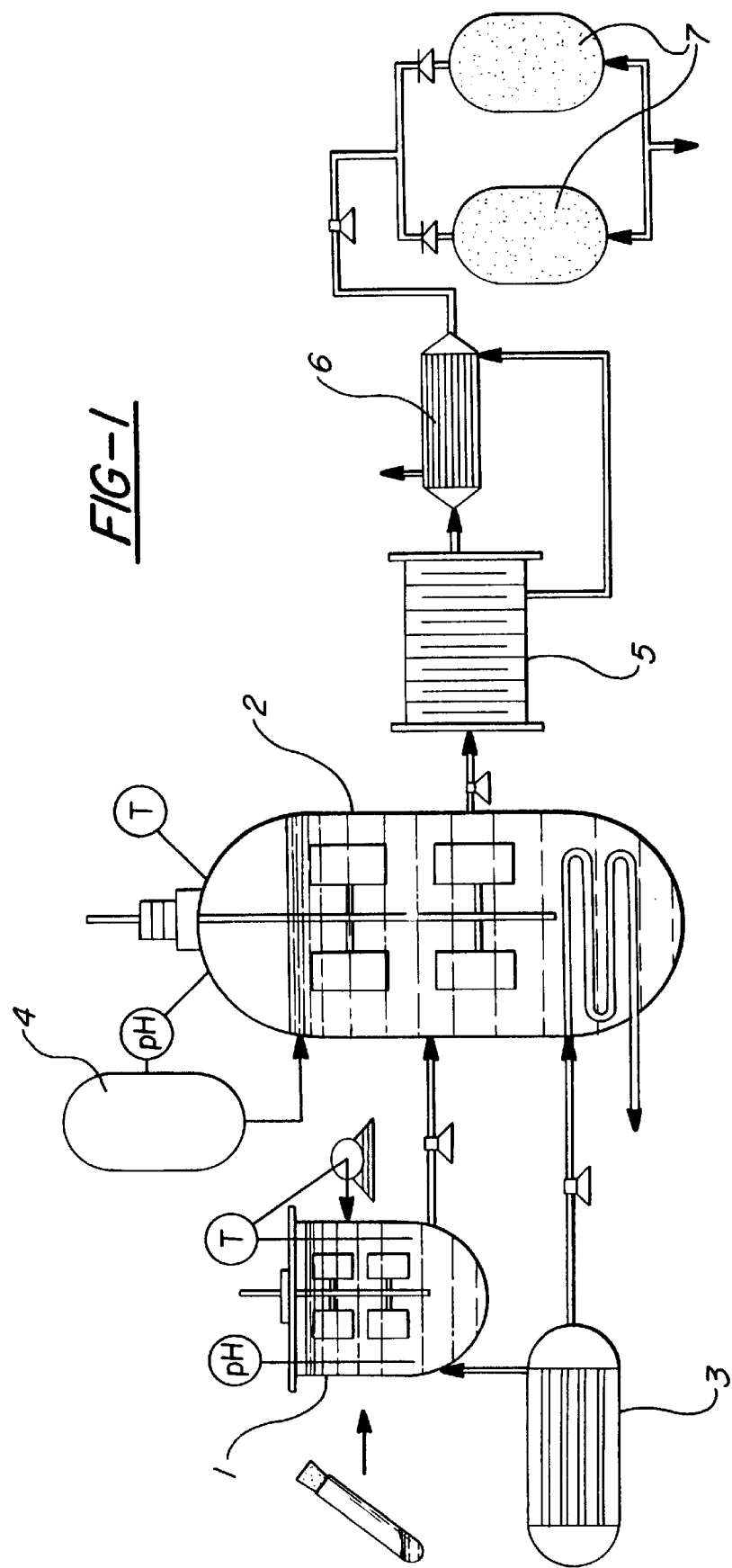
FIG. 1 is a schematic diagram of a system designed for carrying out a procedure of the present invention.

In the studies and experiments conducted for the purpose of developing the procedure described herein, it has been found that *Lactobacillus casei*, which is of the homofermenting type, produces, as the result of the fermentation of lactose, a L-lactic acid in proportions of over 97.5%, depending on the rate at which the same is produced under variable experimental conditions. Some of the most noteworthy experimental conditions being the concentration of the substrate, the temperature, the concentration of the inoculum and the pH of the system.

The procedure of the present invention is essentially characterized by availing of an insemination fermentor in which an insemination of inoculum in a suitable nutrient medium is controlled, said inoculum fermentor being equipped with a steam-supply system which affords the possibility of sterilizing the fermentor, which is additionally equipped with a temperature control system and a pH meter.

The inoculum thus prepared is placed in a second industrial fermentor which is connected to an alkali tank for the purpose of making it possible to maintain the acidity in this fermentor at the optimum levels for the microorganism of the inoculum to grow. For this purpose, a metering pump will be installed on said tank and will be enable by a pH meter employed for the purpose of controlling acidity. During this stage, the fermentation can be achieved using deproteineized whey or untreated whey, by varying the proportion of the lactic acid content within the range of 95%, in the first case of treated whey, and 65%–75%, in the second case. Steam up to 120° C. and 1.2 atmospheres of overpressure must be supplied to the industrial fermentor. Thus, at the same time that the fermentation product is sterilized, the proteins in the whey, albumins and globulins precipitate and are routed to a filter press.

The production of D-lactic or L-lactic isomers depends upon several factors as is inferred from the research conducted for the purpose of developing this process, it having been discovered that the control of the pH and the temperature at which this process is carried out leads to the inoculum inseminated outweighing the microorganisms remaining in the whey. The procedure of fermentation being maintained within the 30° C.–40° C. range, and preferably about 38° C. The pH of the medium falling within the 5–6 range, and preferably being about 5.4. Alkaline base being used to regulate acidity and in particular sodium hydroxide. Also of importance is the nature of the base used in the alkalinization of the system, as is revealed in the results shown in Table I.

TABLE I

Determination of L(+) and D(−) Lactic Acid
Results given in g/l

| Sample | pH | Base | Whey(1) | L(+)lactic | D(−)lactic |
|---|---|---|---|---|---|
| 1 | 1.60 | NaOH | Combined | 18.8 | 0.35 |
| 2 | 1.86 | NaOH | Combined | 21.8 | 1.50 |
| 3 | 1.53 | NH$_4$OH | Combined | 10.9 | 7.70 |
| 4 | 1.49 | Ca(OH)$_2$ | Combined | 2.5 | 15.70 |

(1) considered as being combined whey: (goat's milk + cow's milk)

L-lactic acid production falls within the 93%–96% range when NaOH is used, and totals up to 58% when NH$_4$OH is used, the results being the opposite in the case of using Ca(OH)$_2$, thus making the use thereof highly inadvisable.

The final stage of this process includes the subsequent routing of the fluid from the industrial fermentor through a filter press, a microfilter and some ion-exchange resin columns, these components being installed in this order at the outlet of the main fermentor.

In the aforesaid filter press, the whey proteins, albumins and globulins are separated from the system, proceeding directly in following to eliminating the bacterial cells by routing the liquid from said filter press through hollow-fiber microfilters.

Finally, by means of an ion-exchange system, a product having of pH below 2 and containing no nitrites or toxic metal substances is achieved. The toxicological analysis of the lactic acid thus obtained is shown in Table II.

TABLE II

L-Lactic Acid Toxicological Analysis

Nitrites
None found
Chlorides
2.5 mg/l
Phosphates
3.8 mg/l
Calcium Salts
2.5 mg/l
Magnesium Salts
0.65 mg/l
Toxic Metals
None found
L-Lactic Acid
30.88 g/l
D-Lactic Acid
2.11 g/l
Lactose
12.2 g/l
Proteins
3.01 g/l It is of interest to point out that following the implementation of the inventive procedure, an excellent degree of efficiency is achieved in the production of lactic acid with a total lack of nitrites and of toxic metals, determining that the resulting product is comprised of a high-quality L-lactic acid which can be used as a food preservative.

In order to provide for comprehension of the object of this invention, for illustrative purposes and without a restrictive scope, a description is furnished as to the details of one possible embodiment of the invention, making reference to the attached drawing, on which the diagrammed arrangement of the system designed for carrying out this procedure is shown.

As is shown in FIG. 1, the system is comprised of an insemination fermentor (1), preferably of a capacity within the 5%–10% range of an industrial fermentor (2) for producing lactic acid, to which it is directly connected.

The fermentor (1) is assisted by an agitator system and a steam unit (3) which provides it with the necessary temperature for the operation thereof.

The industrial fermentor (2) is also equipped with a temperature-control system, is connected to an alkali tank (4) installed to control the pH on the interior of the fermentor. This fermentor (2) is equipped with the pertinent agitator, it having been established that the upper blades of the agitator be located at a depth, as regards the surface of the liquid, equivalent to three times the diameter of the agitator.

Following the procedure, it is shown on the drawing that, after the fluid has been processed in the fermentor (2), it is subsequently routed through the filter press (5) and the microfilters (6), to then finally be routed into an ion-exchange circuit (7).

As is shown in FIG. 1, this circuit is comprised of cylindrical receptacles (exchange columns) containing suitable exchange resins. This device affords the possibility of the alternating regeneration of the saturated resin-carrying columns.

All of the above comprises an accurate account of the invention, which must be considered in the broadest, non-restrictive scope thereof, it being possible for the features and qualities of the conventional system and any other accessory conditions which neither detract from nor alter the essential aspect which is the object of claim to be varied.

We claim:

1. A procedure for treating whey produced as a by-product of cheese manufacture, and eliminating the contaminating effects of proteins including albumin and globulins within said whey, on fermentation of said whey and producing enantromerically enriched lactic acid, comprising the steps of: placing said whey into a first inoculum fermentor (1), said first fermentor equipped with a temperature-control system and a pH meter; inseminating of an inoculum comprising a lactic acid producing microorganism in a suitable nutrient medium into said first fermentor so as to yield a fermentation fluid; transferring said fermentation fluid from said inoculum fermentor to a second, larger-sized industrial fermentor (2) upon pH stabilization of said fermentation fluid, said second fermentor being connected, to an alkali tank (4); maintaining acidity of said second fermentor (2) at the optimum levels for the growth of said inoculum, by means of a metering pump set up in said alkali tank under control of a second pH meter installed for regulating acidity; supplying steam of up to 120° C. and 1.2 atmospheres of overpressure to said second industrial fermentor (2) upon pH stabilization independent of acidity regulation so that, at the same time as said fermentation fluid is sterilized, the proteins in said whey, precipitate therein; and routing the proteins of said whey from an outlet in said second fermentor to a filter press (5).

2. The procedure, according to claim 1, wherein said procedure is carried out using untreated whey, and said temperature-control system maintains said first fermentor and said second fermentor within the 30°–40° Celsius range.

3. The procedure, according to claim 1, further comprising the step of routing of said fluid from the outlet of said industrial fermentor (2) consecutively through a filter press (5), a microfilter (6) and ion-exchange resin column (7), thereby yielding L-lactic acid.

4. The procedure according to claim 1 wherein the acidity of said second fermentor is maintained within the 5–6 pH range.

5. The procedure according to claim 4 wherein said metering pump delivers alkaline base to maintain the acidity of said second fermentor.

6. The procedure according to claim 5 wherein the alkaline base is sodium hydroxide.

7. The procedure according to claim 3 wherein the proteins including albumins and globulins within said whey are separated from said fluid in said filter press (5).

8. The procedure according to claim 3 wherein said inoculum is subsequently eliminated from the fluid flowing out of the filter press (5) by passing through said microfilter (6).

9. The procedure according to claim 3 wherein said microfilter is a multiplicity of hollow-fiber microfilters.

10. The procedure according to claim 3 wherein said product having flowed through said ion exchange column is free of nitrites or toxic substances.

11. The procedure according to claim 2 wherein said temperature control system maintains said second fermentor within the 36–40° C. range.

12. The procedure according to claim 2 wherein said temperature control system maintains said second fermentor within the 37–39° C. range.

13. The procedure according to claim 1 wherein the acidity of said second fermentor is maintained within the 5.2–5.6 pH range.

14. The procedure according to claim 1 wherein the acidity of said second fermentor is maintained within the 5.3–5.5 pH range.

15. The procedure, according to claim 1, wherein said procedure is carried out using deproteinized whey, and said temperature-control system maintains said first fermentor and said second fermentor within the 30–40° C. range.

16. The procedure according to claim 15 wherein said temperature control system maintains said second fermentor within the 37–39° C. range.

17. A procedure for treating whey produced as a by-product of cheese manufacture, and eliminating the contaminating effects of proteins including albumin and globulins within said whey, on fermentation of said whey and producing enantromerically enriched lactic acid, comprising the steps of: placing said whey into a first inoculum fermentor (1), said first fermentor equipped with a pH meter and a temperature-control system comprising a steam unit; inseminating of an inoculum comprising a lactic acid producing microorganism in a suitable nutrient medium into said first fermentor so as to yield a fermentation fluid; transferring said fermentation fluid from said inoculum fermentor to a second, larger-sized industrial fermentor (2) upon pH stabilization of said fermentation fluid, said second fermentor being connected, to an alkali tank (4); maintaining acidity of said second fermentor (2) at the optimum levels for the growth of said inoculum at a temperature less than 40° C., by means of a metering pump set up in said alkali tank under control of a second pH meter installed for regulating acidity; supplying steam of up to 120° C. and 1.2 atmospheres of overpressure from the steam unit to said second industrial fermentor (2) upon pH stabilization independent of acidity regulation so that, at the same time as said fermentation fluid is sterilized, the proteins in said whey, precipitate therein; and routing the proteins of said whey from an outlet in said second fermentor to a filter press (5).

* * * * *